United States Patent [19]

Scheuermann et al.

[11] 4,184,985
[45] Jan. 22, 1980

[54] STABLE, AQUEOUS OR AQUEOUS-ALCOHOLIC SOLUTIONS OF FAT-SOLUBLE PERFUME OILS CONTAINING HYDROXYALKYL ETHER-ETHOXYLATES

[75] Inventors: Fanny Scheuermann; Jochen Heidrich, both of Düsseldorf; Martin Bischoff, Gelsenkirchen, all of Fed. Rep. of Germany

[73] Assignee: Henkel Kommanditgesellschaft auf Aktien (Henkel KGaA), Dusseldorf-Holthausen, Fed. Rep. of Germany

[21] Appl. No.: 923,575

[22] Filed: Jul. 11, 1978

[30] Foreign Application Priority Data

Jul. 11, 1977 [DE] Fed. Rep. of Germany ....... 2732218

[51] Int. Cl.² .............................................. C11B 9/00
[52] U.S. Cl. .................................................. 252/522
[58] Field of Search ....................... 252/522, 89 R, 135

[56] References Cited

U.S. PATENT DOCUMENTS 3,758,410  9/1973  Lin ........................................ 252/135

OTHER PUBLICATIONS

Norman G. Gaylord, Polyethers Part 1 Polyalkylene Oxides and Other Polyethers, vol. XIII, Part 1 of High Polymers, Interscience, 1963, pp. 254–257.

N. Schönfeldt, Surface Active Ethylene Oxide Adducts, Pergamon Press, 1969, p. 535.

*Primary Examiner*—Veronica O'Keefe
*Attorney, Agent, or Firm*—Hammond & Littell

[57] ABSTRACT

Stable, aqueous or aqueous-alcoholic solutions of fat-soluble perfume oils, containing hydroxyalkyl ether-ethoxylates of the formula

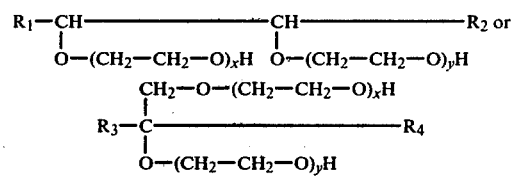

wherein $R_1$ and/or $R_2$ are an alkyl group having 1 to 24 carbon atoms or hydrogen, and $R_3$ and/or $R_4$ are an alkyl group having 2 to 22 carbon atoms or hydrogen, and x and y independently are integers of from 1 to 16, with the proviso that the total of the carbon atoms of $R_1+R_2$ or $R_3+R_4$ is from 2 to 26 and the total of the integers $x+y$ is a value of from 2 to 18.

9 Claims, No Drawings

STABLE, AQUEOUS OR AQUEOUS-ALCOHOLIC SOLUTIONS OF FAT-SOLUBLE PERFUME OILS CONTAINING HYDROXYALKYL ETHER-ETHOXYLATES

FIELD OF THE INVENTION

The invention relates to stable, aqueous or aqueous-alcoholic solutions of fat-soluble perfume oils which contain hydroxyalkyl ether-ethoxylates as dissolving intermediaries.

RELATED ART

Water-soluble perfume oils can be used in many cases for the purpose of perfuming clear, aqueous or low concentration alcoholic cosmetics such as face lotions, after-shave lotions and hair lotions. However, the majority of ethereal perfumes, perfume oils and fragrances are oil-soluble products which can be converted to clear, stable aqueous or aqueous-alcoholic solutions only by the addition of so-called dissolving intermediaries. It is already known to solubilize oil-soluble products by using various dissolving intermediaries such as mono fatty acid esters of polyols such as sorbitol monostearate or various ethylene oxide addition compounds such as polyethoxylated castor oil. A substantial disadvantage of the dissolving intermediaries used up until now is that relatively large quantities have to be added in order to convert the desired and required quantities of perfume oils to a stable, aqueous or low concentration alcoholic solution. A further disadvantage is that their action as a dissolving intermediary is generally very specific and extends only to a limited number of perfume oils.

Therefore, there is a need to develop dissolving intermediaries which, even when added in small quantities, make it possible to prepare clear, stable, aqueous or low concentration alcoholic solutions containing the required concentration of the largest possible number of different perfume oils.

OBJECTS OF THE INVENTION

An object of the present invention is the development of an intermediary which, even in low concentration, can act as a solubilizing agent in the preparation of clear, stable, aqueous or aqueous-alcoholic solutions containing effective concentrations of a great many fat-soluble perfume oils.

Another object of the present invention is the production of a clear, stable, aqueous or aqueous-alcoholic solution of a fat-soluble perfume oil which contains hydroxyalkyl ether-ethoxylates of the formula

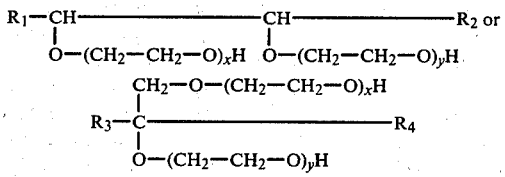

wherein $R_1$ and/or $R_2$ are an alkyl group having 1 to 24 carbon atoms or hydrogen, and $R_3$ and/or $R_4$ are an alkyl group having 2 to 22 carbon atoms or hydrogen, and x and y independently are integers of from 1 to 16, with the proviso that the total of the carbon atoms of $R_1+R_2$ or $R_2+R_4$ is from 2 to 26 and the total of the integers $x+y$ is a value of from 2 to 18.

A still further object of the present invention is the development of an improved process for solubilizing oil- or fat-soluble substances in stable, aqueous or aqueous-alcoholic solutions by using as dissolving intermediaries hydroxyalkyl ether-ethoxylates of the formula

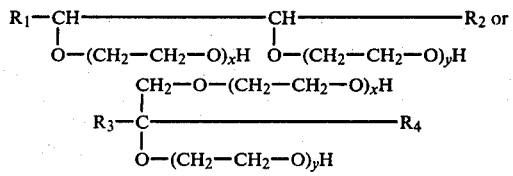

wherein $R_1$ and/or $R_2$ are an alkyl group having 1 to 24 carbon atoms or hydrogen, and $R_3$ and/or $R_4$ are an alkyl group having 2 to 22 carbon atoms or hydrogen, and x and y independently are integers of from 1 to 16, with the proviso that the total of the carbon atoms of $R_1+R_2$ or $R_3+R_4$ is from 2 to 26 and the total of the integers $x+y$ is a value of from 2 to 18.

These and other objects of the invention will become more apparent as the description thereof proceeds.

DESCRIPTION OF THE INVENTION

It has now been found that the above objects can be achieved by employing hydroxyalkyl ether-ethoxylates as dissolving intermediaries to form stable, aqueous or aqueous-alcoholic solutions of fat-soluble substances, especially of perfume oils.

The present invention relates to clear, stable, aqueous or aqueous-alcoholic solutions of fat-soluble substances, especially of perfume oils, which contain an effective amount of hydroxyalkyl ether-ethoxylate dissolving intermediaries of the formula

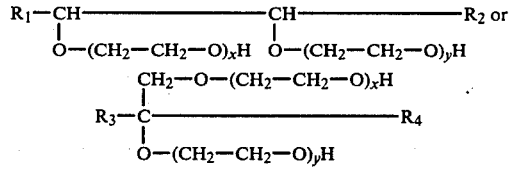

wherein $R_1$ and $R_2$ independently of each other are a member selected from the group consisting of alkyl having 1 to 24 carbon atoms, preferably 12 to 18 carbon atoms, and hydrogen, or $R_3$ and $R_4$ independently of each other are a member selected from the group consisting of alkyl having 2 to 22 carbon atoms, preferably 12 to 18 carbon atoms, and hydrogen, and x and y independently of each other are an integer from 1 to 16, preferably 8 to 14, with the proviso that the total of the carbon atoms of $R_1+R_2$ or $R_3+R_4$ is from 2 to 26, preferably from 6 to 20, and with the further proviso that the total of the integers $x+y$ is from 2 to 18, preferably 8 to 14.

More particularly, the present invention is directed to a stable, aqueous or aqueous-alcoholic solution comprising (1) from 0.1% to 1% by weight, relative to the total weight of the solution, of a fatty substance, preferably a perfume oil, (2) from 0.1% to 20%, preferably 0.5% to 5%, by weight, relative to the total weight of the solution, of hydroxyalkyl ether-ethoxylates of the formula

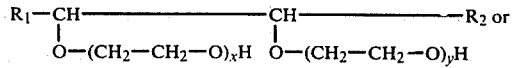

-continued

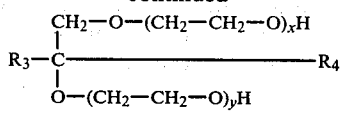

wherein $R_1$ and $R_2$ independently of each other are a member selected from the group consisting of alkyl having 1 to 24 carbon atoms, preferably 12 to 18 carbon atoms, and hydrogen, or $R_3$ and $R_4$ independently of each other are a member selected from the group consisting of alkyl having 2 to 22 carbon atoms, preferably 12 to 18 carbon atoms, and hydrogen, and x and y independently of each other are an integer from 1 to 16, preferably 8 to 14, with the proviso that the total of the carbon atoms of $R_1+R_2$ or $R_3+R_4$ is from 2 to 26, preferably from 6 to 20, and with the further proviso that the total of the integers $x+y$ is from 2 to 18, preferably 8 to 14, and (3) the remainder to 100% by weight of the conventional substances, including the water or water/alcohol solvent, used in said solutions.

The hydroxyalkyl ether-ethoxylates contained in the solutions of the invention can be prepared, for example, in a two-stage synthesis by reacting long-chain epoxides, which can be produced by known methods from olefins of various origins, with ethylene glycol in the presence of alkaline or acid catalysts and by subsequent ethoxylation employing known methods. Hydroxylakyl ether-ethoxylates of this type are described, for example, as constituents of washing-agent formulations in German Offenlegungsschrift No. 1,910,765.

Terminal epoxyalkanes which are particularly suitable for use as starting materials for producing the hydroxyalkyl ether-ethoxylates of the invention are those having chain lengths in the range $C_{12}$–$C_{18}$. Preferred non-terminal epoxyalkanes acting as starting materials are derived from monoolefins having chain lengths in the range $C_{11}$–$C_{14}$ and from monoolefins having chain lengths in the range $C_{15}$–$C_{18}$. These monoolefins have the following chain length distributions:

| | |
|---|---|
| $C_{11}$–$C_{14}$ olefins: | $C_{11}$ olefins, approximately 22 percent by weight, |
| | $C_{12}$ olefins, approximately 30 percent by weight, |
| | $C_{13}$ olefins, approximately 26 percent by weight, |
| | $C_{14}$ olefins, approximately 22 percent by weight. |
| $C_{15}$–$C_{18}$ olefins: | $C_{15}$ olefins, approximately 16 percent by weight, |
| | $C_{16}$ olefins, approximately 32 percent by weight, |
| | $C_{17}$ olefins, approximately 43 percent by weight, |
| | $C_{18}$ olefins, approximately 9 percent by weight. |

A variety of commercially available mixtures of monoolefins are available as starting materials for the preparation of the above-mentioned epoxyalkanes.

Furthermore, mixtures of unbranched and 2-alkyl-branched olefins having a content of non-terminal olefins, such as are prepared during ethylene oligomerization in accordance with the method of Ziegler with subsequent peaking (Ullmann's *Encyclopädie der Technischen Chemie*, Vol. 7, page 210, Verlag Chemie, Weinheim, 1974) can be used as starting materials for the epoxyalkanes.

The following composition represents but one olefin fraction of this type, which can be used in the preparation of the epoxyalkanes.

| | | |
|---|---|---|
| $C_{16/18}$ olefins: | $C_{14}$ olefins, maximum | 2 percent by weight, |
| | $C_{16}$ olefins, approximately | 50 percent by weight, |
| | $C_{18}$ olefins, approximately | 38 percent by weight, |
| | $C_{20}$ olefins, approximately | 10 percent by weight. |

The composition is classified according to structures:
Unbranched, terminal olefins; approximately 60% by weight,
2-alkyl-branched, terminal olefins; approximately 25% by weight,
non-terminal olefins; approximately 17% by weight.

Particularly suitable dissolving intermediaries for use in the clear, stable, aqueous or aqueous-alcoholic solutions of fat-soluble perfume oils of the invention are those hydroxyalkyl ether-ethoxylates derived from terminal $C_{14}$–$C_{16}$ or $C_{16}$–$C_{18}$ epoxyalkanes and from non-terminal $C_{15}$–$C_{18}$ epoxyalkanes, which have 8 to 14 ethylene oxide groups added thereto.

Among the preferred hydroxyalkyl ether-ethoxylates of the invention may be mentioned the products of reaction of $\alpha$-$C_{14/16}$-epoxide+ethylene glycol+9 EO, $\alpha$-$C_{14/16}$-epoxide+ethylene glycol+10 EO, $\alpha$-$C_{14/16}$-epoxide+ethylene glycol+11 EO, $\alpha$-$C_{16/18}$-epoxide+ethylene glycol+8.7 EO, $\alpha$-$C_{16/18}$-epoxide+ethylene glycol+11 EO, $\alpha$-$C_{16/18}$-epoxide+ethylene glycol+13 EO, i-$C_{15/18}$-epoxide+ethylene glycol+9 EO, i-$C_{15/18}$-epoxide+ethylene glycol+10 EO, i-$C_{15/18}$-epoxide+ethylene glycol+11 EO. The above $\alpha$-epoxides are terminal epoxyalkanes and the i-epoxides are non-terminal epoxyalkanes.

Among the suitable fat-soluble perfume oils which can be present in the solutions of the invention are natural or synthetic ethereal oils of all types, such as orange oil, pine oil, peppermint oil, eucalyptus oil, oil of lemons, carnation petal oil, cedar wood oil, bergamot oil, rosemary oil, patchouli oil, lavandine oil, spike oil, rose oil, vetiver oil, fennel oil, aniseed oil, thyme oil, geranium oil, lavender oil, menthol, as well as synthetic, oil-soluble perfume oils from the group of the aldehydes, esters and polyene compounds.

The ratios of the quantity of fat-soluble perfume oil to the quantity of hydroxyalkyl ether-ethoxylate in the clear, stable, aqueous or aqueous-alcoholic solutions in accordance with the invention can vary within wide limits and depend upon the type of perfume oil, the type of dissolving intermediary, the alcohol content and the other accompanying conventional substances which are present in the solution. The hydroxyalkyl ether-ethoxylates can be present in quantities of from 0.1 to 20 percent by weight in the solutions in accordance with the invention, although they will generally be present in quantities of from 0.5 to 5 percent by weight, based on the total weight of the solution. As a general rule, the desired or required quantities of perfume oil are not substantially in excess of or below the limits of from 0.1 to 1 percent by weight, relative to the total weight of the solution. Adjustment of the quantities of dissolving intermediary and fat-soluble perfume oil, as needed to provide a clear, stable, aqueous or aqueous-alcoholic solution, can be readily accomplished by those skilled in the art. The aqueous or aqueous-alcoholic solutions of the invention can also contain, in addition to the dissolving intermediary and perfume oil, conventional quantities of all the customary constituents used in such products.

The clear, stable, aqueous or aqueous-alcoholic solutions of fat-soluble perfume oils in accordance with the invention can be produced in a manner known per se by adding water or an alcohol-water mixture in the desired quantity ratio to concentrates of perfume oil and hydroxyalkyl ether-ethoxylate. The appropriate quantity of water or of water and alcohol for the solutions of the invention can be readily determined by one skilled in the art. Suitable alcohols for use in said solutions are the water-miscible alcohols such as methanol, ethanol and isopropanol. An amount of water or of water and alcohol in the range from about 70-99 weight percent, relative to the total weight of the solution, serves as an example of the amount which might be present in the aqueous or aqueous-alcoholic solutions of the invention.

The solubilizing activity of the hydroxyalkyl ether-ethoxylates of the invention is most evident in purely aqueous solutions or in aqueous solutions containing a low concentration of alcohol, such as, e.g., under 10% by weight. Those aqueous-alcoholic solutions wherein the alcoholic content is from about 1 to 10% by weight of the total solution represent a particularly important embodiment of the invention. However, the alcoholic content of the aqueous-alcohol solutions of the invention can naturally vary over very wide limits, e.g., from only about 1% to 90% or over. The amount of alcohol to be used in the aqueous-alcoholic solutions of the invention will depend on various factors, including the nature of the fat-soluble substance being dissolved and of the dissolving intermediary being used, and the intended application of the solutions.

The invention also includes a process of solubilizing a fat-soluble substance, especially a perfume oil, in a clear, stable, aqueous or aqueous-alcoholic solution by means of a hydroxyalkyl ether-ethoxylate of the formula

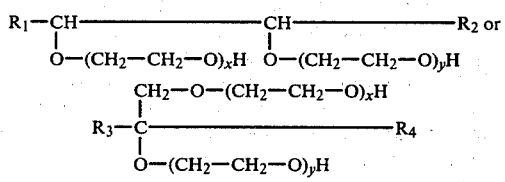

wherein $R_1$ and $R_2$ independently of each other are a member selected from the group consisting of alkyl having 1 to 24 carbon atoms, preferably 12 to 18 carbon atoms, and hydrogen, or $R_3$ and $R_4$ independently of each other are a member selected from the group consisting of alkyl having 2 to 22 carbon atoms, preferably 12 to 18 carbon atoms, and hydrogen, and x and y independently of each other are an integer from 1 to 16, preferably 8 to 14, with the proviso that the total of the carbon atoms of $R_1+R_2$ or $R_3+R_4$ is from 2 to 26, preferably from 6 to 20, and with the further proviso that the total of the integers $x+y$ is from 2 to 18, preferably 8 to 14.

The present invention will now be further described by means of the following Examples which are not to be limitative in any manner.

EXAMPLES

The hydroxyalkyl ether-ethoxylates, to be used in accordance with the invention, were produced in a generally known manner by reacting the corresponding epoxyalkanes with ethylene glycol in the presence of acid catalysts such as $BF_3$ or complexes thereof, or by means of alkaline catalysts such as sodium methylate. The hydroxyalkyl ether produced was subsequently ethoxylated in an autoclave in a conventional manner with the desired quantities of ethylene oxide in the presence of alkaline catalysts.

EXAMPLE 1

The following experiments were carried out in order to test the properties of the ethoxylates of the invention as dissolving intermediaries. A 1% aqueous solution of the perfume oil was prepared in each case. For this purpose, the perfume oil was, in the first instance, agitated together with the respective dissolving intemediary in a specific weight ratio, and sufficient water was subsequently added to produce a 1% solution relative to perfume oil. The ratios of dissolving intermediary:perfume oil chosen were 7:3 and 8:2, corresponding approximately to a 2-fold to 4-fold quantity of dissolving intermediary relative to perfume oil.

The following substances acted as dissolving intermediaries in the experiments:

L 1 α-$C_{16/18}$-epoxide+ethylene glycol+11 EO
L 2 α-$C_{16/18}$-epoxide+ethylene glycol+13 EO
L 3 α-$C_{14/16}$-epoxide+ethylene glycol+7 EO
L 4 α-$C_{14/16}$-epoxide+ethylene glycol+9 EO
L 5 α-$C_{14/16}$-epoxide+ethylene glycol+10 EO
L 6 α-$C_{14/16}$-epoxide+ethylene glycol+11 EO
L 7 i-$C_{11/14}$-epoxide+ethylene glycol+5 EO
L 8 i-$C_{11/14}$-epoxide+ethylene glycol+8 EO
L 9 i-$C_{11/14}$-epoxide+ethylene glycol+10 EO
L 10 i-$C_{15/18}$-epoxide+ethylene glycol+7 EO
L 11 i-$C_{15/18}$-epoxide+ethylene glycol+9 EO
L 12 i-$C_{15/18}$-epoxide+ethylene glycol+10 EO
L 13 i-$C_{15/18}$-epoxide+ethylene glycol+11 EO
L 14 Castor oil+40 EO (comparison substance)

The above substances L1 to L6 are derived from terminal epoxyalkanes while the above substances L7 to L13 are derived from non-terminal epoxyalkanes.

The following 10 ethereal oils of differing composition and polarity acted as the test perfume oil substances in the experiments:

01—Rosemary oil
02—Bergamot oil
03—Cedar wood oil
04—Carnation petal oil
05—Oil of lemons
06—Orange oil
07—Pine oil
08—Peppermint oil
09—Patchouli oil
010—Lavandine oil The properties of the individual aqueous solutions are given in the following Table, wherein x=turbid solution, xx=slightly turbid solution and xxx=clear, stable solution. Furthermore, the Table shows how many different oils a dissolving intermediary is able to dissolve. The larger the number of oils which a dissolving intermediary can dissolve, the higher is its value as a dissolving intermediary in general, since it can be used more universally. Naturally, the results given in the Table can be improved by a higher ration of dissolving intermediary:perfume oil (DI:oil).

TABLE 1

| Dissolving Intermediary | Ratio DI : oil | Oil 01 | 02 | 03 | 04 | 05 | 06 | 07 | 08 | 09 | 010 | Number of Oils dissolved |
|---|---|---|---|---|---|---|---|---|---|---|---|---|
| L 1 | 7 : 3 | xxx | xxx | xxx | xx | xxx | xxx | xxx | xxx | xxx | xx | 10 |
|  | 8 : 2 | xxx | xxx | xxx | xxx | xxx | xxx | xxx | xxx | xxx | xxx |  |
| L 2 | 7 : 3 | xxx | xxx | xxx | xxx | xxx | xxx | x | x | xxx | x | 7 |
|  | 8 : 2 | xxx | xxx | xxx | xxx | xxx | xxx | xx | xx | xxx | xx |  |
| L 3 | 7 : 3 | xxx | xxx | x | xxx | xxx | xxx | xxx | x | x | xxx | 9 |
|  | 8 : 2 | xxx | xxx | x | xxx | xxx | xxx | xxx | xxx | xxx | xxx |  |
| L 4 | 7 : 3 | xx | xx | xx | xxx | xx | xxx | xxx | x | xx | x | 9 |
|  | 8 : 2 | xxx | xxx | xxx | xxx | xxx | xxx | xxx | xxx | xxx | xx |  |
| L 5 | 7 : 3 | xxx | xxx | xxx | xxx | xxx | x | xxx | x | xxx | x | 10 |
|  | 8 : 2 | xxx | xxx | xxx | xxx | xxx | xxx | xxx | xxx | xxx | xxx |  |
| L 6 | 7 : 3 | xxx | xx | xxx | xxx | x | x | xxx | x | xx | x | 5 |
|  | 8 : 2 | xxx | xxx | xxx | xxx | xx | x | xxx | x | x | x |  |
| L 7 | 7 : 3 | x | x | xxx | x | xxx | xxx | x | x | x | x | 5 |
|  | 8 : 2 | xxx | xxx | xxx | x | xxx | xxx | x | x | x | x |  |
| L 8 | 7 : 3 | x | x | x | x | x | x | x | x | x | x | 5 |
|  | 8 : 2 | x | xxx | x | xxx | x | x | xxx | xxx | x | xxx |  |
| L 9 | 7 : 3 | x | x | x | x | x | x | xxx | x | x | x | 2 |
|  | 8 : 2 | x | x | x | xxx | x | x | xxx | x | x | x |  |
| L 10 | 7 : 3 | x | xxx | xxx | x | xxx | xxx | x | x | x | x | 6 |
|  | 8 : 2 | xxx | xxx | xxx | x | xxx | xxx | x | x | xxx | x |  |
| L 11 | 7 : 3 | xxx | xxx | xxx | x | xx | xx | x | xxx | x | xxx | 8 |
|  | 8 : 2 | xxx | xxx | xxx | xx | xxx | xx | xxx | xxx | xxx | xxx |  |
| L 12 | 7 : 3 | xxx | xxx | xxx | x | xx | xxx | xxx | xxx | xxx | x | 10 |
|  | 8 : 2 | xxx | xxx | xxx | xxx | xxx | xxx | xxx | xxx | xxx | xxx |  |
| L 13 | 7 : 3 | xxx | x | xx | xxx | xxx | xxx | xxx | xxx | xxx | xx | 9 |
|  | 8 : 2 | xxx | xxx | xx | xxx | xxx | xxx | xxx | xxx | xxx | xxx |  |
| L 14 | 7 : 3 | x | x | x | x | x | x | x | x | x | x | 0 |
|  | 8 : 2 | xx | xx | xx | xx | xx | xx | x | xx | xx | xx |  |

In order to produce a clear aqueous-alcoholic solution having the same quantity of fat-soluble perfume oil as a purely aqueous solution, the quantities of dissolving intermediary required can naturally be decreased as the alcohol content of the solution increases.

The preceding specific embodiments are illustrative of the practice of the invention. It is to be understood, however, that other expedients known to those skilled in the art or disclosed herein, may be employed without departing from the spirit of the invention or the scope of the appended claims.

Wherever used in this specification, the term "fat-soluble" means "soluble in a vegetable or animal fat or oil".

We claim:

1. Clear, stable, aqueous or aqueous-alcoholic solutions of a fat-soluble ethereal perfume oil, consisting essentially of (1) from 0.5 to 5% by weight, relative to the total weight of the solution, of a hydroxyalkyl ether-ethoxylate intermediary of the formula

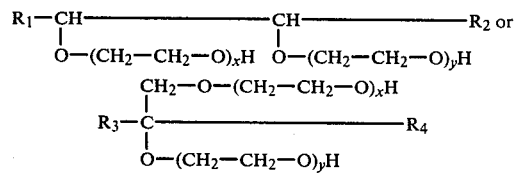

wherein $R_1$ and $R_2$ independently of each other are a member selected from the group consisting of alkyl having 1 to 24 carbon atoms, or $R_3$ and $R_4$ independently of each other are a member selected from the group consisting of alkyl having 2 to 22 carbon atoms and hydrogen, and x and y independently of each other are an integer from 1 to 16, with the proviso that the total of the carbon atoms of $R_1+R_2$ or $R_3+R_4$ is from 2 to 26, and with the further proviso that the total of the integers $x+y$ is from 2 to 18, (2) from 0.1 to 1% by weight relative to the total weight of the solution of a fat-soluble etheral perfume oil, wherein the amount of said ester-ethoxylate intermediary is at least four times the amount of said perfume oil, (3) from 0 to 10% by weight of a water-miscible alcohol, and (4) the remainder to 100% by weight of the conventional substances used in said solutions including water where the amount of water or water and alcohol is from 70 to 99% by weight, relative to the total weight of the solution.

2. The solution of claim 1, wherein $R_1$ and $R_2$ independently of each other are alkyl having 12 to 18 carbon atoms, and $R_3$ and $R_4$ independently of each other are alkyl having 12 to 18 carbon atoms, and x and y independently of each other are an integer from 8 to 14, with the proviso that the total of the carbon atoms of $R_1+R_2$ or $R_3+R_4$ is from 6 to 20, and with the further proviso that the total of the integers $x+y$ is from 8 to 14.

3. The solution of claim 1, wherein the hydroxyalkyl ether-ethoxylates are derived from unbranched and 2-alkyl branched terminal $C_{14}$-$C_{16}$- or $C_{16}$-$C_{18}$-epoxy alkanes and have 8 to 14 ethylene oxide groups adducted thereto.

4. The solution of claim 1, wherein the hydroxyalkyl ether-ethoxylates are derived from non-terminal $C_{15}$-$C_{18}$ epoxy alkanes and have 8 to 14 ethylene oxide groups adducted thereto.

5. The solution of claim 1, wherein the hydroxyalkyl ether-ethoxylates are the products of reaction from a member selected from the group consisting of
α-$C_{14/16}$-epoxide+ethylene glycol+9 EO,
α-$C_{14/16}$-epoxide+ethylene glycol+10 EO,
α-$C_{14/16}$-epoxide+ethylene glycol+11 EO,
α-$C_{16/18}$-epoxide+ethylene glycol+8.7 EO,
α-$C_{16/18}$-epoxide+ethylene glycol+11 EO,
α-$C_{16/18}$-epoxide+ethylene glycol+13 EO,
i-$C_{15/18}$-epoxide+ethylene glycol+9 EO,
i-$C_{15/18}$-epoxide+ethylene glycol+10 EO, and
i-$C_{15/18}$-epoxide+ethylene glycol+11 EO.

6. The solution of claim 1, wherein the hydroxyalkyl ether-ethoxylates are the products of reaction from a member selected from the group consisting of α-$C_{16/18}$-epoxide+ethylene glycol+11 EO,
α-$C_{16/18}$-epoxide+ethylene glycol+13 EO,
α-$C_{14/16}$-epoxide+ethylene glycol+7 EO,
α-$C_{14/16}$-epoxide+ethylene glycol+9 EO,
α-$C_{14/16}$-epoxide+ethylene glycol+10 EO,
α-$C_{14/16}$-epoxide+ethylene glycol+11 EO,
i-$C_{11/14}$-epoxide+ethylene glycol+5 EO,
i-$C_{11/14}$-epoxide+ethylene glycol+8 EO,
i-$C_{11/14}$-epoxide+ethylene glycol+10 EO,
i-$C_{15/18}$-epoxide+ethylene glycol+7 EO,
i-$C_{15/18}$-epoxide+ethylene glycol+9 EO,
i-$C_{15/18}$-epoxide+ethylene glycol+10 EO, and
i-$C_{15/18}$-epoxide+ethylene glycol+11 EO.

7. A process of solubilizing a fat-soluble ethereal perfume oil in a clear, stable, aqueous or aqueous-alcoholic solution comprising adding water or an alcohol-water mixture to a concentrate of said perfume oil and a hydroxyalkyl ether-ethoxylate of the formula

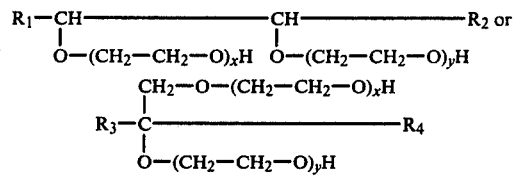

wherein $R_1$ and $R_2$ independently of each other are a member selected from the group consisting of alkyl having 1 to 24 carbon atoms, or $R_3$ and $R_4$ independently of each other are a member selected from the group consisting of alkyl having 2 to 22 carbon atoms and hydrogen, and x and y independently of each other are an integer from 1 to 16, with the proviso that the total of the carbon atoms of $R_1+R_2$ or $R_3+R_4$ is from 2 to 26, and with the further proviso that the total of the integers x+y is from 2 to 18, to thereby form an aqueous or aqueous-alcoholic solution.

8. The solution of claim 1, wherein the water-miscible alcohol is methanol, ethanol, or isopropanol.

9. The solution of claim 1, wherein the conventional substance is water.